United States Patent [19]

Woodbridge, III

[11] 4,007,010
[45] Feb. 8, 1977

[54] BLISTER PLANE APPARATUS FOR TESTING SAMPLES OF FLUID

[76] Inventor: Richard G. Woodbridge, III, 40 North Road, Princeton, N.J. 08540

[22] Filed: Apr. 2, 1976

[21] Appl. No.: 672,916

Related U.S. Application Data

[63] Continuation-in-part of Ser. No. 485,548, July 3, 1974, abandoned.

[52] U.S. Cl. .................. 23/253 R; 23/253 TP; 23/259
[51] Int. Cl.² ............. G01N 27/00; G01N 31/00; G01N 33/00
[58] Field of Search ............ 23/230 R, 253 R, 259, 23/230 B, 253 TP; 195/127 R

[56] References Cited

UNITED STATES PATENTS

| | | | |
|---|---|---|---|
| 3,036,894 | 5/1962 | Forestiere | 23/253 TP X |
| 3,476,515 | 11/1969 | Johnson et al. | 23/230 R |
| 3,552,928 | 1/1971 | Fetter | 23/253 TP |
| 3,620,678 | 11/1971 | Gurgan et al. | 23/253 R |
| 3,689,224 | 9/1972 | Agnew et al. | 23/253 TP UX |
| 3,697,227 | 10/1972 | Goldstein et al. | 23/253 TP |
| 3,713,779 | 1/1973 | Sirago et al. | 23/253 TP X |

Primary Examiner—Morris O. Wolk
Assistant Examiner—Michael S. Marcus
Attorney, Agent, or Firm—Behr & Woodbridge

[57] ABSTRACT

A sample of fluid is processed in a sandwich-like processing card comprising an upper layer and a lower layer, at least one of which layers has pliable characteristics. The space between the two layers is completely filled with a liquid preferably having certain grease-like characteristics so as to exclude all contaminating air. The liquid filled space is referred to as the activity plane. In operation, a sample of the fluid to be tested in the form of a small droplet is injected into the activity plane so as to constitute a blister. The blister may be moved throughout the activity plane by an external pusher of appropriate geometry. The pusher acts upon the blister by pressing on and moving along the pliable layer. Also located in the activity plane are a plurality of chemical, physical or detecting process stations to which the blister may be moved by the pusher as desired. The entire apparatus preferably is rectangular in shape but also may be circular or cylindrical.

30 Claims, 16 Drawing Figures

U.S. Patent  Feb. 8, 1977  Sheet 1 of 2  4,007,010
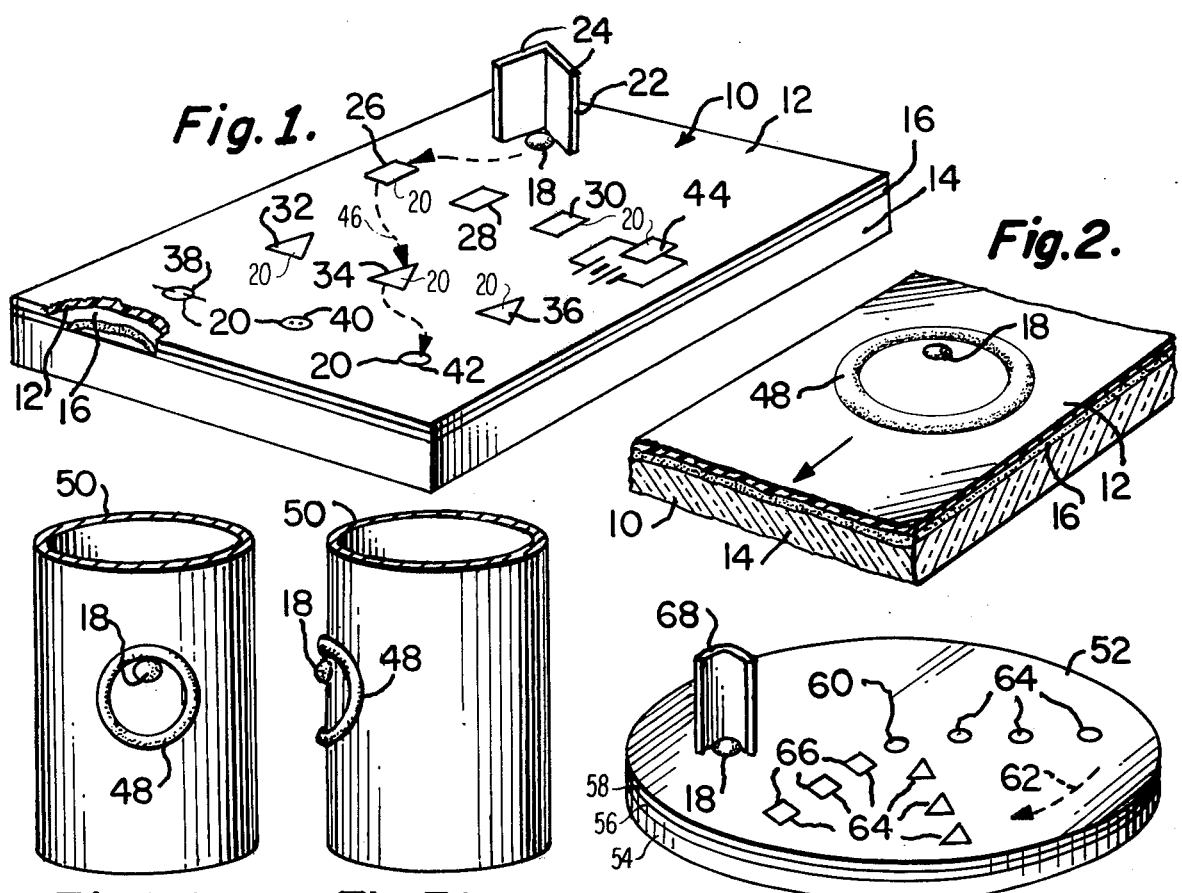
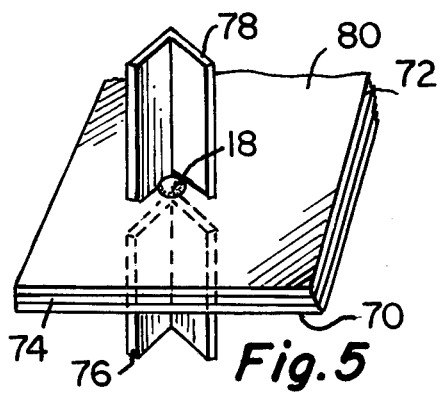
Fig.3A.   Fig.3B.
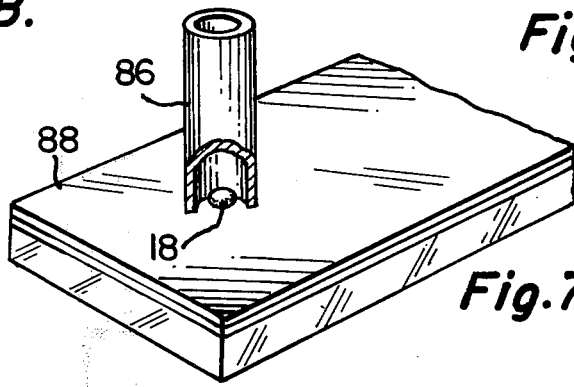
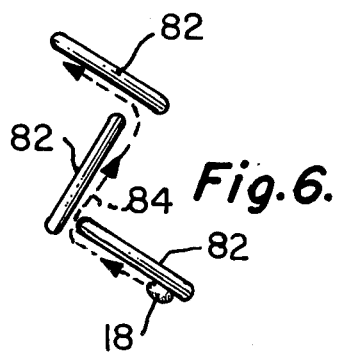
Fig.5
Fig.6
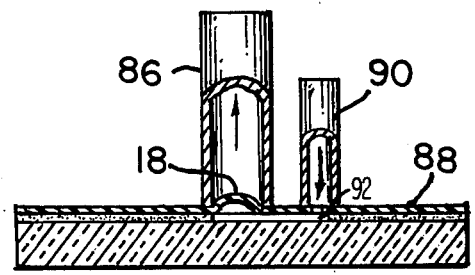
Fig.7A.
Fig.7B.

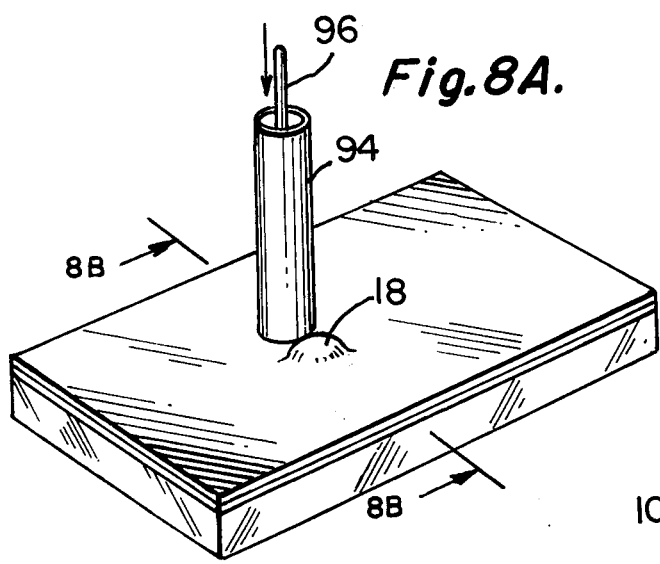
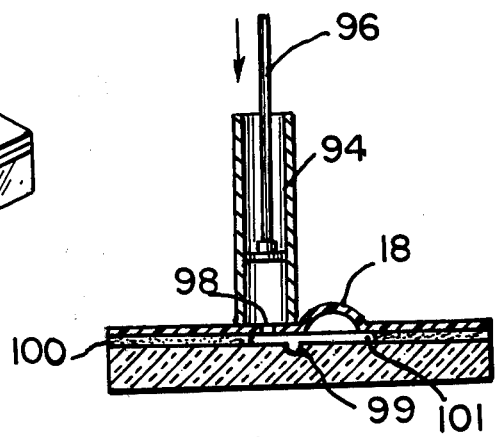
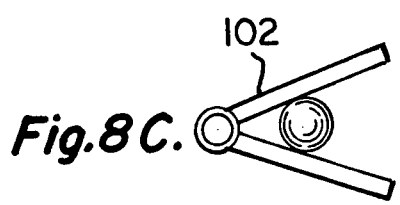
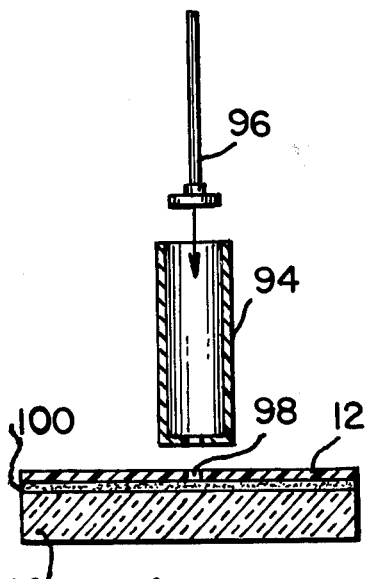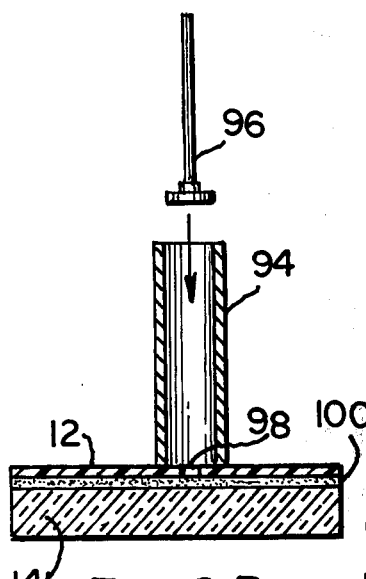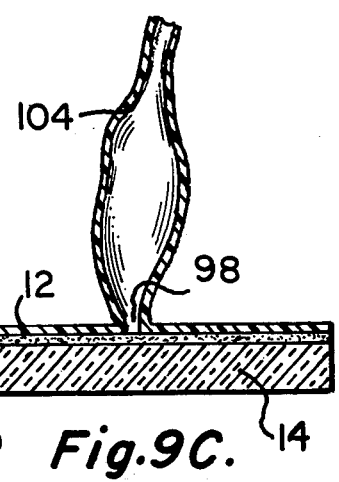
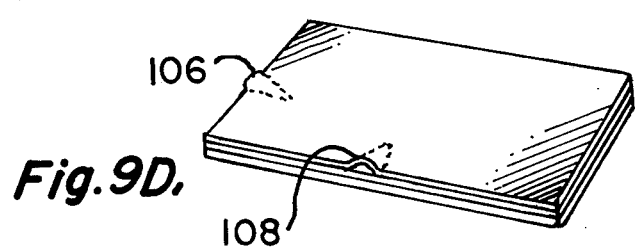

BLISTER PLANE APPARATUS FOR TESTING SAMPLES OF FLUID

CROSS REFERENCE TO RELATED APPLICATIONS

This application is a continuation-in-part of my co-pending application entitled "Analytical Test Strip Apparatus"; Ser. No. 485,548 filed July 3, 1974, now abandoned. The disclosures in said co-pending application are incorporated herein by reference.

BACKGROUND OF THE INVENTION

1. Field of the Invention

This invention relates to an apparatus and method for performing a variety of chemical, physical and detecting operations upon a small sample of fluid or fluid-like material.

2. Description of the Prior Art

A description of relevant prior art can be found in my co-pending application Ser. No. 485,548 described above and incorporated by reference.

Several different techniques are popularly known for the analysis of liquid samples. One such device is the continuous flow analyzer of the type produced by the Technicon Corporation. Continuous flow analyzers are well known to those of ordinary skill in the art but have the general disadvantage that they are relatively expensive, bulky in size and nondisposable.

The encapsulation of a reagent in a plastic package is known in the related art. For instance, part of the technique employed by the well known Polaroid Land Camera is to contain a chemical reagent in a plastic pouch and then, by applying roller pressure to it, force the pouch to rupture and spread its content over a sheet of chemically treated paper or between sheets of thin plastic for the purpose of developing the same. Moreover, the desalination of water has been accomplished in emergencies by introducing sea water into a pouch containing a reactive silver containing substance and then squeezing the water out through a filtering medium into the mouth.

Several different types of prefabricated plastic analyzers are described in the following United States patents: Johnson et al, U.S. Pat. No. 3,476,515; Blackburn et al, U.S. Pat. No. 3,497,320; Johnston et al, 3,544,705; Schwartz, U.S. Pat. No. 3,660,033; Agnew et al, U.S. Pat. No. 3,689,224; Goldstein, et al, U.S. Pat. No. 3,697,227; Sharpiro, 3,713,780; and Nighohossian et al, U.S. Pat. No. 3,715,189. The foregoing can be broadly described as being plastic devices containing one or more reaction chambers into which chemical agents or samples may be added. In Johnson et al, the agents are added by rupturing an internal compartment filled with reagent. In Schwartz, the reagent or indicator is located in the reaction chamber itself.

Of special interest is Forestiere, U.S. Pat. No. 3,036,894. Forestiere discloses a "Method of Using Testing Containers" in which a linear chain of small, joined plastic reaction vessels, which are hollow chambers or pouches or bags containing predetermined amounts of reagents are connected together between two pieces of plastic material in strip form. A sample of material is introduced into the top hollow chamber and then squashed through the subsequent chambers in linear order by means of a pair of squeeze rollers. The reagents in the respective hollow chambers are separated one from another by an adhesive barrier "of relatively small area" which will break open when the matters in the chambers are squeezed strongly against it.

The present invention differs from the foregoing prior art in several major respects. Most importantly, the present invention has nothing to do with hollow containers, chambers, pouches or bags such as in the Forestiere patent. The present invention dispenses entirely with containers, chambers, pouches and bags.

In the Forestiere patent reactions are constrained to a pre-set, linear order. That is the sample, after being put in the top bag, is constrained to enter into the following chamber and react with the reagent there and then must enter into the next chamber, and so on in predetermined order. In the present invention the domain of the sample may be conceived as all pathways possible between the various stations. There is no sequence of activities constrained by the geometry of the system.

The Forestere device is generally unsatisfactory in operation as may be seen from the following consideration. Upon crushing or squashing the entrance chamber the sample is squeezed into the first hollow reaction chamber and then reacts with the reagent therein. The entire contents of the first chamber is then crushed into the second pouch to react with the reagent there. The combined contents of the first and second pouches are then squeezed into the third and so on. This may cause the adhesive barriers down the chain to explode open far in advance of the sample being squashed through the chain of chambers and cause the final chamber which is sealed at its end to distend and balloon. The effect may be mitigated by having compressible reagents or having the chambers largely filled with air. To prevent excessive ballooning appropriate venting mechanics would necessarily have to be provided. However, vents would largely mitigate against the processing of noxious materials or virulent bacteria, viruses, etc.

The Forestiere device involves not only chambers in a fixed linear array but also predetermined amounts of reagent in fixed positions with which to react the sample. In the present invention the reagents of interest may be in fixed position and be of predetermined amount but may also be in any position desired, even mobile of themselves and of any desired amount because in the present invention a blister may be not only of the material being tested but a second (or third, or fourth, etc.) blister may be a blister containing the reagent. Such a reagent blister may be pushed around, separated into portions, etc. at the will of the experimenter.

The present invention has an additional advantage over the invention described in my co-pending application Ser. No. 485,548 in that a "blister" may be moved in two dimensions along an activity plane. In the prior art the sample is typically constrained to move in one particular channel or in a plurality of fixed channels. According to the Applicant's invention, the moving blister forms its own channel.

SUMMARY OF THE INVENTION

It has been discovered that a droplet of fluid, hereafter referred to as a "blister" may be caused to move within a space comprising a sandwich-like device including a pliable layer and a firm back-up layer. The space between the two layers is filled with an inert fluid immiscible with the fluid of the blister. The blister may be selectively moved by the use of a suitable pusher acting by pressing down upon the blister from outside of the pliable layer.

While the droplet or blister does form a somewhat raised area on the plastic layer, the mechanics of the movement of the blister appear to be more complicated than merely pushing a protuberance. It was discovered that when pressure is exerted through a pliable layer upon a liquid beneath, that the liquid beneath will form a ridge-like distention around the device causing the pressure, i.e., around the pusher exerting the pressure. By imparting motion to the pusher this distention takes on many of the characteristics of a wave. A droplet of fluid immisible with the inert liquid filling the sandwich has been found to "ride" the curvature of the advancing, front slope of the "wave" so produced, rather like the way a person on a surfboard will ride an ocean wave. This phenomena lends itself in most excellent fashion to the handling and processing of liquid droplets and has led to the development of an apparatus for analytical purposes which is the subject of the present invention.

Briefly described, the present invention, according to the preferred embodiment, comprises an apparatus for testing a sample of fluid. The apparatus includes a sandwich-like processing device having a front layer and a back layer, at least one of which is relatively pliable. Both layers define a two dimensional activity plane in which is located a plurality of chemical, physical and/or detecting stations. The chemical, physical and detecting stations are collectively known as process stations. The activity plane is filled with an inert liquid medium which contacts the two layers, thus helping to keep them together and which the medium forms the lateral or side walls of the mobile blister. In operation, a small sample of fluid to be tested immiscible with the liquid of the activity plane is introduced into the activity plane. The sample droplet forms a slight "bulge" or "blister" which can be moved around the activity plane from outside by a variety of "pusher" or "propelling" devices. The force of the propelling means against the blister causes the liquid of the activity plane to permit a passage to be formed therethrough and allows the blister to be moved forward as directed by the pusher. As the blister moves forward the pusher causes the liquid behind the blister to reseal the two layers. Accordingly, the blister forms its own channel. In this manner the blister may be moved in two dimensions in such a fashion as to selectively pick and choose process stations with which it may wish to make contact. According to alternative embodiments of the present invention, the activity plane may be circular or cylindrical or made to conform to some other two or three dimensional geometry.

The present invention has several advantages over the known prior art. In particular it has the advantage of being able to perform relatively accurate volumetric analyses in a contamination-free atmosphere. Additionally, due to its two dimensional character, it permits a greater variety of experiments to be conducted than was heretofore known to be possible with devices having distinct channels. These and other features of the present invention will appear clearly from the following drawings and detailed description.

BRIEF DESCRIPTION OF THE DRAWINGS

FIG. 1 illustrates a blister processing apparatus according to the preferred embodiment of the present invention.

FIG. 2 illustrates the use of a ring type blister pusher in the context of a flat processing card.

FIG. 3a is a front elevational view of a saddle shaped ring type blister pusher adapted to conform to the surface of a cylindrical blister card.

FIG. 3b is a side view of the embodiment illustrated in FIG. 3a.

FIG. 4 illustrates a circular blister card.

FIG. 5 illustrates a lower V shaped pusher that can be used to match an upper V shaped pusher for the purpose of propelling a blister.

FIG. 6 illustrates pusher blades arranged in a herringbone configuration.

FIG. 7a illustrates a tube type pusher which may also be used to induce blisters by means of a vacuum.

FIG. 7b is a cross-sectional view of the tube pusher 86 of FIG. 7a and sample input tube 90.

FIG. 8a illustrates a method of forming a blister by injecting the sample liquid into a pore in the processing card.

FIG. 8b is a cross-sectional view of the method and apparatus illustrates in FIG. 8a.

FIG. 8c is a combined injector and pusher incorporating the general concepts illustrated in FIGS. 8a and 8b.

FIGS. 9a, 9b and 9c illustrate alternative embodiments of the blister forming method and device illustrated in FIGS. 8a, 8b and 8c.

FIGS. 9d illustrates an embodiment in which the sample of fluid is end fed into the activity plane through a port.

DETAILED DESCRIPTION OF THE INVENTION

During the course of this description, like numbers will be used to designate like elements according to the different drawings of the invention.

The invention according to a preferred embodiment thereof is illustrated in FIG. 1. A processing card 10 comprises a top layer 12 and a bottom layer 14 separated by a thin liquid or semi-liquid like medium 16. The liquid 16 comprises an inert flowable medium which adheres slightly to the two layers thereby helping to keep them together but functioning primarily as the lateral or side walls of the blister. Lower layer 14 comprises a glass plate but may comprise a flexible material in the context of other embodiments. Upper layer 12 preferably comprises a thin film of plastic such as polyethylene, polyperfluorethylene, polyvinylchloride or co-polymers of vinylchloride and vinylidene chloride. It is important that the upper layer 12 be sufficiently thin to allow the formation of a blister between it and the glass plate 14.

According to FIG. 1, a blister of fluid 18 is shown trapped between upper layer 12 and lower layer 14. The area between the upper layer 12 and the lower layer 14 may be thought of as an activity plane which contains the blister 18, the inert liquid medium 16 and a plurality of process stations 20. According to the preferred embodiment of the present invention, the medium 16 effectively excludes all air from the process stations 20 by substantially filling up the space between the layers 12 and 14. A pusher 22 is illustrated directly behind blister 18 in FIG. 1. According to the preferred embodiment, the pusher 22 has a V shape. The pusher may be made of metal or plastic or of a rubber material and is adapted to slide across the upper surface of the upper layer 12. A lubricant may be added to the surface of the layer 12 to improve its sliding characteristics. In operation, the pusher is positioned so that the blister is cradled in the arms 24 of the V. In this matter, the pusher retains the blister and causes it to maintain its shape and integrity. The pusher 22 is a propelling means adapted to cause the forward movement of the blister 18. The blister 18 is propelled forwardly when the pusher 22 is pressed against the surface of the upper layer 12 and the V is then moved in the direction desired. Arms 24 of the pusher 22 prevent the blister 18 from spreading out. The inert liquid medium 16 will part under the forward pressure of the blister 18 but according to the preferred embodiment will reseal directly behind the blister 18 as the pusher 22 moves across the surface of the upper layer 12. In this manner, the channel formed by the forward progress of the blister 18 is immediately resealed as the pusher 22 moves forward. By changing the direction in which the pusher 22 moves, it is possible to manipulate the blister to any one of a plurality of desired process stations 20 or to another blister.

During the course of the foregoing description, it will be appreciated by those of ordinary skill in the art that the present invention does not include chambers, fixed channels or channels with fixed walls. There is also no fixed direction in which the blister must move.

The present invention comprehends a variety of different stations 20. For example, station 26 might be a small amount of chemical reagent. Station 28 might by a similar small amount of dilutent. Station 30 may be yet another reagent or diluent. Stations 26, 28, 30 and 44 are collectively referred to as chemical process stations. Stations 32, 34 and 36 are locations at which some physical processing step might occur. For example, at station 34, the fluid in the blister might be subjected to a filtering step in a manner similar to that described in my co-pending application Ser. No. 485,548, or Station 34 comprises a warming or cooling area or an area in which the sample is irradiated. Stations 38, 40 and 42 are collectively referred to as detecting stations. This is because the results of the reaction in the chemical and/or physical process stations are determined in the detecting stations. Several different types of detecting functions are possible. For example, at station 42 the layers 12 and 14 may be of sufficient transparency to allow the blister at station 42 to be subjected to optical analysis, such as the measurement of its refractive index or turbidity. Alternatively, reagents could be used to measure the properties of the processed blister. Station 44 indicates a location at which the blister may be subjected to an electrical current.

The path transversed during a typical process is illustrated in phantom as line 46. According to this example, the blister 18 is moved along path 46 so that it first reacts with the reagent of chemical process station 26. After that reaction, the blister 18 moves through physical process station 34 where it is filtered and then on to detecting station 42 where it is subjected to optical analysis. Clearly other paths could have been traversed by the blister depending upon the type of analyses to be performed. For example, the blister could have moved from station 28 to station 32 to station 38. Alternatively, the blister could move to two or more chemical, physical or detecting stations before the analysis is complete. For example, the blister could move from station 28 to 30 then from 30 to 36 to 40 to 38. The path traversed by the blister is dependent solely upon the analysis sought to be performed.

In FIG. 2, a ring shaped pusher is illustrated in the act of propelling a blister 18 in a forward direction. A ring shaped pusher has an advantage over V shaped pusher 22 in that is completely contains the blister 18. In some circumstances, it may be desirable for the blister 18 to completely fill out the volume defined by the periphery of the ring pusher 18.

The ring shaped pusher 48 of FIG. 2 is shown in the context of a flat, rectangular process card 10. The ring pusher could be of a circular or saddle shape and it should be sufficiently elastic to conform to the contour of the underlying surface. If a flat, planar process card 10 is employed, it may be desirable to include in the card 10 some indexing points such as holes, dots or lugs which would improve the ease of machine positioning and handling. These points not illustrated would make possible the use of a coordinate system for location purposes. While the process card 10 is shown to be rectangular in shape, it will be understood that one dimension of the rectangular could be considerably longer than the other. In such a case, a strip or ribbon-like process card would be formed. It is possible that such a strip could be wound on a reel or stored and handled in a cassette-like device. Such an invention is described in substance in my co-pending application previously referred to. If a strip-like process card is employed, the pusher mechanism might comprise a pair of drawing rollers. According to one embodiment, it would be possilbe to wind the strip on the side of a revolving wheel or the strip may be wound as a helix on the surface of a cylinder. The pusher mechanism then could stay stationary while the wheel or cylinder revolves. In this manner, the blister would be caused to traverse the length of the strip and pass through the various chemical, physical or detecting stations. In FIGS. 3a and 3b, the ring shaped pusher 48 is shown in the context of a process card 50 having a cylinderical shape. FIG. 3b is a side view of the embodiment illustrated in FIG. 3a. According to this embodiment, the ring pusher 48 has a saddle type shape which conforms to the curved geometry of the process card 50. In this manner, the ring completely contains the blister 18. The blister 18 can be caused to move in any direction over the surface of the process card 50.

A circular "phonograph record" type of process card 52 is illustrated in FIG. 4. Process card 52 comprises a platen 54, an inert liquid medium 56 and a circular elastic top layer 58. In this respect, the structure of process card 52 is identical to the structure of process card 10 illustrated in FIG. 1. Process card 52 is equipped with a center spindle hole 60 and is adapted to ride on a turntable in the direction illustrated by phantom arrow 62. A plurality of process stations 64 are located with respect to spindle hole 60. Additionally, the device may require additional art work in the form of coodinate grills, identification points for optical readings and perforations for automatic manipulation, filling, mechanical readings, etc. Such perforations though not illustrated might be in the body of the process card 52 itself or along the edge and side thereof. In a similar manner, the process card 52 might be adapted to include lugs or similar projections which could fit into matching detents in a turntable to insure the accurate registration between the turntable and the process card 52. The use of lugs could make a central spindle hole unnecessary.

In operation, the circular process card 52 is caused to rotate in the direction of phantom arrow 62. Blister 18 is formed in the activity plane and is propelled forwardly by a U shaped pusher 68. The apparatus illustrated in FIG. 4 differs from other embodiments in that the process card moves relative to the user while the blister 18 stays relatively stationary. Therefore, the stations come toward the blister rather then vice versa. During the course of rotation, the blister is caused to move through a plurality of chemical, physical and detecting or indicating stations in the manner previously described. It will be appreciated by those of ordinary skill in the art that a physical station may come before a chemical station or that no indicating or detecting stations will be employed at all. In another mode of use, it is possible to move the blister 18 inwardly towards the spindle hole 60 as it describes a spiral path towards the center. Accordingly, the circular process card can be used for a plurality of concentric experiments or as one long continuous experiment as the pusher mechanism 68 is drawn towards the center spindle hole 60. Though a U shaped pusher is illustrated, it will be appreciated that other types of pushers such as the ring type pusher illustrated as element 48 in FIGS. 2 and 3 might not be employed also. According to the preferred embodiment, the lower layer or platen 54 consists of a rigid material. In this manner, the device is more readily adaptable to a turntable. The circular process plane is preferably formed in a manner similar to plane 10 by placing a sealent 56 om the lower platen 54 and then sandwiching the stations 64 and 66 between the lower platen 54 and the upper layer 58.

The lower layer or platen described in FIGS. 1–4 may be made of any suitable metal, plastic, glass or film. If the lower layer 14 or 54 is made of film, then it would be highly desirable to provide the lower layer with some kind of back support. FIG. 5 illustrates an embodiment 80 of the present invention in which the lower layer 70 comprises an elastic compressable film similar or identical to the top layer 72. The inert liquid medium is designated as element 74. Because the lower layer 70 is flexible, it is necessary to give it support in order to move the blister forward. This support is provided in FIG. 5 by a lower V shaped pusher 76 which compliments or matches the upper pusher 78. Pushers 76 and 78 are similar to the V shaped pusher 22 illustrated in FIG. 1. The distance between the pusher 76 and 78 is approximately the depth of the process plane 80. Consequently, any blister that forms will be pinched between the two pushers 76 and 78. By drawing the pushers forward, it is possible to propel the blister 18 in any manner desired. While the lower layer 14 or 54 is illustrated as being solid, it will be understood that the lower layer could comprise laminated material such as a plastic and a metal, or a glass and a platic base, etc.

The upper layer illustrated as element 12 in FIG. 1 and element 58 in FIG. 4 preferably comprises any one of a wide variety of flexible plastic films such as polyethylene, polyvinylchloride, polyfluoroethylene, polyvinylidine chloride, etc. Alternatively, a metal or metallic foil could be used or a thin elastic or rubber membrane could be employed for the same purpose. Such upper layers might comprise materials having the characteristics of clear adhesive tape or labels having pressure sensitive adhesives.

Though not illustrated, it may be desirable in certain applications to erect permanent barriers extending from the upper to the lower layers of the processing plane. Such barriers can be introduced, for example, by welding or permanently cementing areas of two layers together. The barriers thus formed would aid in directing the motion of a blister or could serve as an integral part of a processing station. In the case of plastic materials, it is possible to construct barriers of the sort just described by heat welding. The barriers could also be of very fine hairs or filaments.

The liquids illustrated as element 16 in FIG. 1 and as element 56 in FIG. 4 generally wants to be reaction inert, immiscible and non-emulsifiable with regard to the fluid (gas or liquid) found in the blister and the material constituting the upper and lower layers. It should be understood by those skilled in the art that the sealant liquid includes those materials, and indeed it is preferred to use those materials which have high viscosity and which might be considered to have pseudo-solid status such as greases, pressure sensitive adhesive agents and soft waxes. It should be understood that no limitation of actual viscosity is considered to be critical to this invention since the actual viscosity will vary in accordance with the materials utilized and the temperature at which the reactions contemplated are carried out. Having a view therefore, to the foregoing conditions that the sealant liquid and the fluid in the blister shall be inert and imiscible with reference to each other, suitable sealants include liquids having a hydrocarbon skeleton which may be cyclic or acyclic, aromatic or aliphatic. These materials may, if desired, contain as substituents, substantially reactive groups such as oxygenated groups, for example, hydroxy, keto, hydrocarboxy (acid), alkanol carboxy or aroylcarboxy (ester), halo, and the like as well as substantially inert groups for example, oxo, alkyl, aryl, or aralkyl.

Also included in this general organic category are perhalogenated liquids and silicones. In the case of the silicones the substituent groups utilized may be similar to those above.

Also included as suitable sealant liquids for more specialized purposes, particularly where it is desired to operate at slightly elevated temperatures, are liquid or low melting metals such as mercury, or low melting alloys such as Woods metal, liquid metaloids, and liquid sulfur, as well as liquid salts.

It will be recognized by those skilled in the art that use of these somewhat more exotic liquid media may require the use of special temperature conditions as well as the use of special temperature resilient materials which form the pliable layer under which the reactions of the present invention are to be carried out. Clearly, the material of the pliable layer must be temperature stable at the desired temperature and chemically inert with respect to the agents constituting the liquid medium.

In addition to the liquids set forth above, greases, pressure sensitive adhesive agents, and waxes of more complex chemical constitution may be utilized provided that they meet with the aforementioned basic criteria of inertness and imiscibility with respect to the fluid in which the reaction is to take place. Also, included as a suitable sealant medium is water and water containing materials dissolved therein. In the case of waxes, the lower layer or platen could be coated with a wax which by pressure could cause the upper layer of film to adhere to the lower layer. This is the phenomenon exhibited by a child's writing slate wherein the top layer can be removed to cause the writing to disappear. In addition the inert fluid medium in the sandwich and the fluid of the sample must also bear another relation with regard to each other in that the fluid of the sample does not displace the inert liquid comprising the sandwich filling. This phenomena is referred to as as "inversion".

The blister 18 described in FIGS. 1-4 contains only the fluid to be analyzed. The fluid constituting the blister which will either be, per se, the subject of the reaction in the system of the present invention or will act as a carrier therefor may be either in the liquid or gaseous state.

It will be understood by those skilled in the art that the fluid must be substantially compatible with respect to the aforesaid liquid medium. That is to say that it will not react chemically with said medium, or be physically effected thereby such as dissolving therein. It should, of course, be understood that these criteria of chemical and physical inertness cannot be considered as absolute. Nevertheless, the degree of interaction shall be sufficiently low as to cause no significant variation in the phenomena to be measured or the reactions to be carried out in the system as a whole.

Thus, for example, where petroleum jelly is the sealant liquid, the reactions contemplated may be carried out in aqueous fluids or strongly polar oxygenated organic solvents such as alkanols, or alkanoic acids. On the other hand, substantially non-polar organics such as hexane or benzene or halogenated organics such as chloroform, methylene chloride or the like would not be suitable since they tend to dissolve the jelly. It is also inadvisable to utilize the fluids which tend to have a surfactant action on the sealant medium. That is to say that part of the chemical constituent of the fluid would tend to dissolve in the sealant liquid. Further, care must be taken to avoid emulsification which may sometimes tend to occur when the reactions are carried out in strongly alkaline medium using a substantially inert organic sealant liquid such as petroleum jelly.

It will of course be understood by those skilled in the art that where, for example, aqueous media are employed as the sealant liquid, the working fluid constituting the blister should be similarly inert with respect thereto. Thus, the working fluid may be an organic liquid such as hexane, but not an organic liquid such as an alkanol for example ethanol; a gas for example, air, oxygen, or nitrogen, but not a gas such as chlorine or sulfur dioxide; metal such as for example, mercury, but not a metal such as sodium or potassium.

Those skilled in the art will recognize that certain sealant liquid/working fluid combinations will constitute borderline cases with respect to compatibility, but the existence of such borderline cases does not in any way detract from the general applicability of the method.

According to alternative embodiments of the present invention, the blister may contain solid materials which aid the analytical process. For example, the blister may contain a ball bearing like sphere or another suitable object such as a roller which acts as a "tent pole" to keep the blister from collapsing thus greatly enhancing its volume. In this manner, the ball bearing is surrounded by the fluid under examination. With a ball or roller of metallic material, it may be possible to control the movement of the material and the bubble by magnetic means. The blister may also include a small "boat" to contain the sample. As the blister is moved forwardly, the boat would be caused to slide along therewith. In some cases, it may be desirable to use the fluid in the blister as a medium for transporting solid particles. Under such circumstances, the solid particles would be the materials to be analyzed and the fluid merely acts as a neutral conveying means.

The pusher can have a variety of shapes, several of which have already been described. According to FIG. 1, the pusher 22 may have a V shape including a pair of arms 24 which cradle the blister 18. In a similar manner, a ring 48 is disclosed in FIGS. 2, 3a and 3b which completely encircles the blister 18. Under some circumstances, a half circle or a half ring may be employed to achieve the same results. According to FIG. 4, the pusher 68 is shown to be a U shaped element with a semi-circular bottom end. A U with a square bottom could also be appropriate under some circumstances, for example, to spread the blister over the surface of a wide area. In addition to the foregoing pusher embodiments, there are other types of pushers which may be desirable for specific applications. For example, the blister could be propelled by means of a "doctor" blade or roller. A similar technique is described in my co-pending application, Ser. No. 485,548. However, since the blister is not constrained to move in any one particular direction, it may be necessary to move the blade or roller first towards one side and then towards the other to achieve a resultant forward motion of the blister without the blister escaping sideways. The pusher can also take the form of a shaped pad. Under certain circumstances, it may be desirable to cause the pusher to vibrate the blister to enhance mixing of the fluid sample within the blister. If the blister is confined by two parallel walls or barriers, it can be propelled forwardly by means of a simple roller or doctor blade.

According to FIG. 6, the pusher 82 comprises a series of blades arranged in a herringbone pattern. As the blister 18 is propelled forwardly by the blades 82 along the path illustrated by the phantom arrow 84, the blister is also caused to roll sideways off one blade and then caused to be picked up by the following blade, etc.

According to FIG. 7a, the pusher 86 is illustrated as comprising a hollow tube. Alternatively, a pusher of this sort could comprise the end of a funnel or cone. By means of a hollow pusher such as illustrated as element 86, it is possible to subject the blister 18 to the pressure found inside the hollow portion of the pusher. For example, air or hydraulic pressure could be introduced into the tube and so used to manipulate the blister 18. Rapidly varying pressure inside tube 86 can be used to vibrate and mix the fluid in the blister 18. Under some circumstances, it may be desirable to separate the pressurizing fluid in the pusher from the elastic upper layer by means of a suitable elastic diaphragm. Such a diaphragm could be drawn into the tube by reducing the pressure therein.

According to FIG. 7a, the tube type pusher 86 can also be used as a means of inducing a blister. FIG. 7b shows the pusher 86 of FIG. 7a is cross section and in combination with a sample input tube 90. The sample of fluid is introduced into sample input tube 90. The sample is then drawn out of the sample input tube 90 through channel 92 by the blister 18 formed within tube 86. In this manner, a uniform blister of fixed dimensions can be readily formed for use in subsequent processing steps.

According to alternative embodiments of the present invention, the pusher consists of two circles which effectively touch each other at a nip point. The blister 18 then can be cradled in the nip and so confined as it is propelled forwardly without loss of integrity. The two circles could comprise the ends of two rods which, for example, are not necessarily of the same dimension. One or both said rods could be caused to rotate or one might be in rotation with respect to the other. The rotation of the rods aid in the mixing and propelling of the blister 18. The same effect as previously described can be achieved from the use of two beveled discs, for example, two truncated columns which touch each other. The beveled discs would be free to rotate or be driven, if so desired. In such a case, the propelling motion of the pusher is achieved by pressing the conical surfaces into the elastic, flexible upper membrane layer. Additionally, a flexible, rubbery roller having a slightly curved axis can be employed as a pusher. The geometry of such a pusher would act to conserve the integrity of the blister.

According to the preferred embodiment of the invention illustrated in FIG. 1, a plurality of chemical process stations are indicated as elements 26,28,30 and 44. These stations cold just as well be physical process stations in the context of other analytical applications. For example, station 26 could be primarily a filtration station. However, according to this preferred embodiment, the chemical stations illustrated as square elements 26,28,30 and 44 could consist of the following types of stations. According to one embodiment, the chemical stations could comprise a predeposited bleb of reagent such as a microgram pimple. Similarly a bleb of liquid could be employed to act as a solvent or a dilutent. Alternatively, the chemical stations indicated as squares could have been previously saturated with the chemical to be added.

In addition to containing particular reagents, the chemical process stations can be areas having special chemical properties. For example, they may be areas permeable to gas or liquid from the outside. To transport materials into or out of certain process stations, a hole or pore can be situated in the area of the station so that the reagent, whether it be liquid or gas, can be injected directly into the blister. As illustrated in FIG. 1, the chemical process station might comprise an electrolytic cell illustrated as element 44. In such a cell, processes involving electrolysis may be performed.

As a companion to the chemical process stations illustrated, a bleb containing a reagant may be caused to move into the blister by osmosis or be caused to soak out of the blister in the same manner. The chemical process stations can comprise an area containing a culture medium or nutrients where the incubation of living organisms can be achieved.

A chemical process station may also consist of an area of the inert liquid, particularly if the liquid is a grease or wax which contains the reagent desired. This could be in the form, for example, of a band of grease through which the blister is moved thereby picking up the reagent which, for example, could be an indicator.

A desired reagent could be carried in a blister itself. The reaction would be induced by pushing the blister of sample and the reagent blister together. A reagent blister would lend itself to parting or separating so that only the desired amount of reagent could be united with the blister of sample.

The volume of a blister, whether it is a blister of sample or a blister containing reagent can in general be determined with considerable accuracy by determining its thickness with a micrometer and measuring its area and then multiplying the two together.

According to FIG. 1, the physical process stations 32, 34 and 36 are illustrated as triangles. As described in my co-pending application, Ser. No. 485,548, such as a physical operation station could comprise a location where filtration takes place. Alternatively, the filtration can be selective so as to separate only specific components of the blister for further analysis or detection. A physical operation station can also include a blister spliting mechanism. Such a blister splitting device could comprise an inverted Y or V which would serve to divide a blister into two parts. For example, as a blister is propelled against the point of an inverted V, it would be separated into two portions. In other embodiments, the physical operation station could comprise an agitation station where the blister may be agitated for mixing purposes. Alternatively, a physical operation station could comprise a settling station where heavy particles of material can be caused to precipitate out of the solution of the blister sample. The invention also comprehends a draw-off station where the fluid in the blister is drawn or pushed out of the system for processing from the outside. Such a draw-off station might also include a means for permitting the subsequent re-injection of the drawn-off sample. Additionally, the process station can include an internal pit of definite volume which would remove from the passing blister a specific volume of fluid. Other stations could provide locations for cooling, heating, irradiating, crystalizing, absorption, agitating, washing, extracting, centrifuging, drying, phase change, etc.

As illustrated in FIG. 1, station 38, 40 and 42 comprise measurement indicating stations. In the context of this application, the terms measurement station, indicating stations and detecting stations are used interchangably. These stations can be thought of as read-out locations which can serve to perform a variety of different functions. For example, station 38 comprises a conductivity cell with two or more electrodes attached thereto. By applying a measurable current across the station 38, it is possible to determine from the exterior of the process card 10 the conductivity of the blister sample. A measurement station could also contain a reagent which serves as an indicator. For example, the indicator might comprise a material which visually illustrates the pH of the blister sample. The pH could also be measured by electrodes attached to the cell in the same manner as illustrated by the conductivity cell 38. Measurement station 40 contains an array of indicator dots which individually responds to different characteristics of the blister sample. The measurement station could also include provisions for an optical cell in which the optical characteristics of the fluid (for example, fluorescence, index or fraction, turbidity, etc.) could be determined. Furthermore, a measurement station can contain particles of different specific gravity which by sinking or floating would show the specific gravity of the fluid in the blister sample. An optical read-out position might also be provided with light transmitting optical fibers.

Thus far, the invention has been described in terms of pre-prepared stations for performing chemical, physical or measuring functions. However, an important aspect of the present invention consists of a station or station whose function may be altered at will. One embodiment of this concept would consist of removing a circular area of the platen and fitting the resulting hole with a tight-fitting piston and plunger. A bleb of the desired reagent is then placed on the top, flat surfaces of the plunger. The piston is then pushed into the hole so that its upper surface would be flush with the surrounding surface of the platen. A blister when propelled to this newly formed station would react with the reagent as it would in a preformed station. An alternative embodiment of this concept would be to have blebs of reagents on discs. The discs could be cemented into holes (using beveled edges) or over holes, in one of the laminar layers, in the platen. Therefore, part of the present invention comprehends the use of blister processing planes which have provisions for one or more of the above described universal blister processing stations.

There are several techniques by which a blister to be processed might be formed. According to one embodiment, a certain position on the blister processing plane may be thought of as being devoted to the blister formation operation. This area may be at any convenient location. For example, according to the embodiment of FIG. 1, the blister formation location is located near chemical operation station 26. In a circular card, the blister formation area might preferably be near the center of the card with various process stations situated radially therefrom. A variety of methods can be employed to introduce the sample between the upper and lower layers so as to form the blister. According to one method, the fluid may be introduced through a small hole in one of the layers using, for example, a hypodermic needle which passes through a self-closing seal. In this way, a predetermined, pre-measured amount of fluid may be introduced into the blister. FIGS. 8a and 8b illustrate an alternative method of blister injection. According to FIG. 8a, a hollow tube 94 is fitted internally with an injector piston 96. The injection cylinder 94 is situated directly above a small injection pore 98 which communicates the interior of injection cylinder 94 with the activity plane 100. The blister is formed by placing the sample in the interior cavity of the injection cylinder 94 and then forcing it, by means of injection piston 96, through the injection pore 98 into the interior of the activity plane 100. As the sample passes into the activity plane 100, it forms a bulge or blister 18 as illustrated in cross-section in FIG. 8b. One advantage of this technique is that the sample introduced can be accurately measured according to the displaced volume in the injection cylinder 94. FIG. 8O also illustrates a small channel 101 such as shown in the lower layer extending from the area within the cylinder and under the wall at the cylinder. The channel facilitates the passing of the sample fluid to an appropriate location outside the immediate injection area. A subchannel 99 within channel 101 keeps channel 101 open even if partially collapsed by forces exerted upon cylinder 94. FIG. 8c illustrates a combination injector and pusher apparatus 102. The injector/pusher 102 combines the features of an injection cylinder 94 and a V shaped pusher 92 such as described with reference to FIG. 1. According to this embodiment, the blister may be formed and subsequently propelled by the same device. In order to protect the processing card from contamination, it may be desirable to cover the injection pore 98 with tape or some other form of removable seal. The blister formed by the foregoing methods may be separated from the pore by moving the blister away from the situs of formation. A blister is formed by the foregoing method because the pressure on the interior of the injection cylinder 94 is greater than the pressure in the activity plane 100. FIG. 9a, 9b and 9c illustrate other blister forming apparatus. According to FIG. 9a, the injection cylinder 94 may be a separate unit which must be selectively positioned directly above the injection pore 98. In FIG. 9b, the injection cylinder 94 is illustrated as being integral with the upper layer 12 of the blister processing card. This particular embodiment has the advantage that it is securely communicated with the injection pore 98 but has the disadvantage that it can be used at only one predetermined location. FIG. 9c illustrates in cross-section a bag type of blister former which protrudes above the upper layer 12 of the process card. The bag type blister former 10 can alternately be thought of as a pocket or blister. The walls of the bag 104 are integral extensions of the upper layer 12. According to the preferred embodiment, the walls at the top of the bag 104 are tightly cemented so as to exclude all contamination. To open the bag and insert blister sample, the top of the bag would be snipped off and the material inserted therein. The top of the bag would then be pinched and the walls of the bag squeezed inwardly so as to propel the blister sample through the injection pore 98 and into the activity plane 100. The bag type blister former 104 can be modified to include convenient, protruding tabs to facilitate easier opening of the bag. Alternatively, the pocket could be opened by squeezing its edges thereby causing the bag to pucker. A sample may be introduced into the reaction plane by "end feeling". According to this technique, the blister is formed by inserting a hypodermic needle or thin hollow blade into the activity plane between the upper layer 12 and the lower layer 14. The sample fluid is then forced through the hypodermic needle or hollow blade, thereby forming a blister at the pocket formed. Alternatively, a pre-formed pocket can be formed between the upper layer 12 and the bottom layer 14 as illustrated in FIG. 9d. A sample of fluid may be introduced into the empty pocket 106 or 108 and then advanced through the activity plane by a pusher. This is another form of end feeding.

With certain analyses, it may be desirable to transfer a blister sample from one processing card to another. This can be done, for example, by the withdrawing the fluid from a blister using a hypodermic needle and then re-injecting the sample to form a blister in another processing card. In order to avoid air contamination, one processing card with the blister can be placed directly over the card to which the blister sample is to be transferred. The hypodermic needle can then be used to penetrate the blister of the top card and withdraw its contents. Once the top blister has collapsed, the hypodermic needle would be forced lower into the bottom blister processing card and the contents of the hypodermic needle would be thereafter forced into the activity plane of the lower blister processing card. In this manner, the blister of the top card is transferred to the bottom card without removing the syringe from the cards. Since the blister sample is never exposed to air, there is minimal risk of contamination by this method. Rather than providing blister transfer by means of an external device such as a hypodermic needle, transfer may be affected at a suitable station by providing a channel through which the material may be forced by pressure exerted upon the blister. According to this embodiment, an injection pore in one processing card must be aligned directly with an injection pore in a second processing card. Alternatively, the fluid could be transferred from one processing card to another by means of suction. This could be accomplished by using a simple hole or by means of a short length of hypodermic tubing sharpened at both ends so as to appropriately puncture one layer of one processing card and one layer in the second processing card. In this manner the activity planes of both processing cards are directly communicated by the hypodermic tubing. The tubing could pass through a layer which comprises a plate, sheet, foil, etc. which serves to hold the piece of tubing and which may provide a working surface.

It will be appreciated by those of ordinary skill in the art that the present invention has the distinct advantage of having a variable volume which conforms to the size of the blister and amount of reagent positioned at the process stations of the blister processing card. This is important because if the cavity housing the blister were larger than the volume of the blister sample, then clearly the excess volume would contain contaminating materials. In this and other respects, the present invention is believed to be a significant improvement over prior art analytical devices.

EXAMPLE I

An activity plane was prepared by placing a flat piece of transparent glass 7 inches by 5 inches on a flat surface to act as the lower layer, rigid platen and carrier of the stations of the sandwich apparatus or card. About 1 inch from the bottom and about 2 inches apart, two tiny crystals of ammonium thiocyanate were affixed to the glass plate using beneath each one a tiny drop of a nitrocellulose base household cement which was allowed to dry thoroughly. The two little blebs were then coated with petroleum jelly. In the approximate center of the plate was placed a ¼ gram portion of petroleum jelly. On top was placed a piece of transparent polyethylene film 9 inches by 7 inches, the film being larger than the glass plate so that it could be held in fixed position relative thereto. The polyethylene film used was 0.001 inches thick. Using a doctor blade on the outer surface of the polyethylene sheet, the petroleum jelly was spread over the entire glass plate including the blebs of ammonium thiocynate taking care to see that there was no air entrapment, particularly around the blebs or reagent, and no cavities or any places not filled with the petroleum jelly. The petroleum jelly constituted the filling of the sandwich. It was 0.0005 inches thick.

In the top end of the sandwich, using a fine knife blade slipped between the polyethylene sheet and the glass, a small pocket was opened. Using fine tweezers, a speck removed from the eye of a patient was put into the little entrance port to which was then added a drop of 5% C.P. hydrochloric acid and allowed so to set for some minutes. The pocket was carefully closed so as to retain the drop which was moved down into the reaction plane proper using a V shaped pusher where it formed a "blister". A period of about a 2 weeks intervened. Subsequently, using the V shaped pusher, the blister was moved through the petroleum jelly filling the reaction plane to the bleb of ammonium thiocyanate. An intense red color immediately developed which showed that the speck of unknown was iron and not zinc which it otherwise might have been. The dilute hydrochloric acid used was tested for iron in a similar manner using a new entrance port and the other bleb of ammonium thiocyanate and found to be free of iron.

EXAMPLE II

A sheet of transparent polyvinyl chloride-polyvinylidene chloride copolymer about 8 inches by 10 inches was laid on a flat rigid surface. This sheet was 0.0005 inches thick. On the sheet was placed several drops of sterilized sea water. The sheet was covered with a second sheet of the same film. Using a doctor blade on the outside of the upper film the liquid water was spread so as to completely fill the space between the two films. Using a hypodermic needle, a small droplet of S.A.E. 20 motor oil was introduced through the upper film into the water filled space between the two films. The water film was about 0.0005 inches thick. The blister thus formed was then moved away from the entrance position using as a pusher the fire polished end of a piece of glass tubing which was of such size as to hold within the circular area of its end the blister of S.A.E. 20 oil.

The blister was moved to a position on the flat rigid surface which had a window through it through which shown a beam of ultraviolet light. The blister did not show significant florescence indicating the absence of multiring aromatic compounds.

The blister was then subdivided into five portions by gently pressing and appropriately manipulating a dull knife blade upon the blister through the upper film.

The first of the five blisters was pushed to an area in which a very small speck of metallic silver previously had been deposited. The other four blisters were moved to diverse, separate positions. Using a hypodermic needle three of the blisters were innoculated with differing strains of soil bacteria. This was done using a very fine hypodermic needle and then moving the blisters away from the puncture holes. The entire apparatus was then suspended in the ocean in a suitable container in the presence of a small amount of sterile sea water. After three months submersion, it was found that the speck of silver film was very tarnished, indicating the presence of considerable sulfur in the oil. On pushing the three remaining blisters, it was found that no longer was the sea water inert with respect to the oil because as the blisters were moved about an emulsification process became obvious which indicated that the bacteria had caused a breakdown of the oil. An indication of the degree of the tendency to emulsify which had developed could be obtained by moving each blister a standard distance, here 4 inches, and observing the turbidity which had developed. In such a manner, it was possible to determine the most active strain of bacteria toward the oil of the composition under examination. The blister which was not innoculated served as a control.

EXAMPLE III

A 0.0005 inch thick sheet of transparent polyester film 8 inches by 10 inches was laid on a flat rigid surface. Upon this were placed two drops of warm liquid, nutrient agar medium about two inches apart. The agar was permitted to cool and solidify. A ¼ gram portion of petroleum jelly was placed in the approximate center of the piece of film.

A second sheet of the same polyester film was prepared as follows. Using a cork borer, a hole ½ inch in diameter was cut in such a position that when it was subsequently placed upon the bottom piece of film the hole registered with one of the solid blobs of nutrient agar. Into the hole so formed was cemented a ½ inch circle of GE silicone film of the type highly permeable to oxygen (cut from a larger sheet using the same cork borer). This sheet of film was then placed upon the bottom sheet of film. Using a doctor blade over the outside of the top film, the petroleum jelly was spread throughout the space between the two films taking care that the agar nutrient stations were completely engulfed without cavity formation and without air entrapment. The thickness of the petroleum jelly was 0.0005 inches.

It was found convenient at this point to cut from the above sandwich apparatus a 5 inch by 7 inch portion containing portions of the two sheets of film, the filling petroleum jelly and the agar stations and then to seal the edges. After sterilizing by suitable radiation, the packets or cards could be conveniently stored for many months.

To use, a small piece of corner was snipped off and a drop of the serum to be tested was introduced by squeezing the edges of the corner and pushing in the end of a glass medicine dropper which had been drawn out to a fine point. Using a V shaped pusher, the blister so formed was moved away from the entrance atrium. The blister was then divided by appropriately pressing with a dull blade and then using the V shaped pusher, one portion was moved to one agar station and the other to the other. After standing at room temperature 48 hours, bacterial growth under the silicone membrane area was noticably advanced with respect to the other. This indicated that the bacteria involved were aerobic.

It will be clear to those of ordinary skill in the art that modifications may be made in the basic invention without departing from the spirit of the invention. For example, the sandwich may have hermetically sealed or welded edges for sterility reasons and may be stored and handled independent of the back-up platen and pusher. The inert liquid can be colored, opaque or made fluorescent. The whole apparatus may be edge lighted or lighted by ultraviolet light. A blister may at any time be frozen, the sandwich opened and the material constituting the blister removed. It is clear that this invention may be adapted to the analysis of solid matters by providing a suitable entrance port or aperture into which a particle or particles of solid can be introduced and to which, for example, a blister of solvent could be pushed.

While the invention has been particularly shown and described with reference to a preferred embodiment thereof, it will be understood by those skilled in the art that various changes in form and detail may be made therein without departing from the spirit and scope of the invention.

I CLAIM:
1. A blister processing apparatus for testing a sample of fluid, said apparatus comprising:
   a blister processing card having an upper level and a lower layer, said layers defining a two dimensional activity plane therebetween through which said sample may pass, at least one of said layers having pliable characteristics;
   a blister forming means for introducing a blister sample into said acitivity plane;
   a plurality of process station means located in said activity plane;
   an exterior pusher means for propelling said sample through said activity plane; and
   an inert liquid medium located within said activity plane, said medium being strong enough to prevent the movement of said blister sample in said activity plane solely under the influence of gravity but weak enough to allow said blister sample to pass through said activity plane under the influence of said pusher, there being sufficient medium in said plane so as to substantially exclude contaminants from said plurality of station means,
   wherein said sample is introduced into said activity plane by said blister forming means and then moved selectively around said two dimensional activity plane under the influence of said pusher acting through said pliable layer from outside of said apparatus thereby causing said blister sample to pass through said plurality of process station means substantially without contamination.

2. The apparatus of claim 1 wherein said blister processing card is substantially flat and rectangular in shape.

3. The apparatus of claim 2 wherein sid pusher means comprises a circular ring.

4. The apparatus of claim 1 wherein said blister processing card is cylindrical in shape.

5. The apparatus of claim 4 wherein said pusher means comprises a saddle-shaped ring.

6. The apparatus of claim 1 wherein said blister processing card is circular in shape and adapted to rotate around a center.

7. The apparatus of claim 6 wherein said pusher means comprises a U shaped means.

8. The apparatus of claim 6 wherein said lower layer is relatively rigid and said upper layer is relatively pliable.

9. The apparatus of claim 1 wherein said pusher means has a V shaped cross section.

10. The apparatus of claim 9 wherein said pusher means comprises two pusher elements each having a V shaped cross section wherein one pusher element is located directly above and in contact with the upper layer of the blister processing card and the other element is located directly below and in contact with the blister processing card in the same orientation as the pusher located above.

11. The apparatus of claim 1 wherein said pusher means has a herringbone type cross section.

12. The apparatus of claim 1 wherein said blister forming means comprises a hollow tube capable of evacuation.

13. The apparatus of claim 1 wherein said blister forming means comprises a hollow sample injection cylinder having a cavity communicated at one end to the activity plane and adapted at the other end to receive an injection piston,
   wherein said sample of fluid may be placed within said injection cylinder and forced into said activity plane by said injection piston thereby forming a blister within said activity plane.

14. The apparatus of claim 1 wherein said pusher means and blister forming means are integrally connected together.

15. The apparatus of claim 13 wherein said sample injection cylinder is integral with said upper layer of said blister processing card.

16. The apparatus of claim 13 wherein said sample injecting cylinder and said upper layer of said blister processing card are separate elements.

17. The apparatus of claim 1 wherein said blister forming means comprises a pliable bag type means communicated at one end with the activity plane of said blister processing card and adapted to receive said sample at the other end of said bag,
wherein said sample may be introduced into said bag, sealed therein, said subsequently forced into said activity plane by applying pressure to the walls of said bag.

18. The apparatus of claim 1 wherein one of said plurality of process station means includes at least one chemical operation station.

19. The apparatus of claim 18 wherein said chemical operation station is a chemical reagent.

20. The apparatus of claim 18 wherein said chemical operation station includes means for performing electrolysis on said blister sample.

21. The apparatus of claim 1 wherein one of said plurality of process station means further includes at least one physical operation station.

22. The apparatus of claim 21 wherein said physical operation station comprises a filtering station.

23. The apparatus of claim 1 wherein one of said plurality of process station means comprises a detecting operation station.

24. The apparatus of claim 23 wherein said detecting operation station comprises a location where one of said layers is sufficiently transparent to allow optical measurements to be taken of said sample.

25. The apparatus of claim 23 wherein said detecting operation station includes a reagent therein which changes color according to a given specific property of the blister sample.

26. The apparatus of claim 23 wherein said detecting operation station includes a plurality of indicator dots each being selectively sensitive to characteristics of said blister sample.

27. The apparatus of claim 23 wherein said detecting operation station includes means for determining the electrical conductivity of said blister sample.

28. The apparatus of claim 1 wherein said blister forming means comprises a port in the edge of said card for communicating the activity plane to the area external to the card.

29. A blister processing card for testing a sample of liquid in the shape of a blister, said card comprising:
an upper layer and a lower layer, said layer defining a two dimensional activity plane therebetween through which said sample may pass, at least one of said layers having pliable characteristics;
a plurality of process station means located in said activity plane; and,
an inert liquid medium located within said activity plane, said medium being strong enough to prevent the movement of said blister sample in said activity plane solely under the influence of gravity, but weak enough to allow said blister sample to pass through said activity plane unde the influence of an external force, there being sufficient medium in said plane so as to substantially exclude contaminants from said plurality station,
wherein said sample is introduced into said activity plane and then moved from outside of said card selectively around said two dimensional activity plane thereby causing said blister sample to pass through said plurality of process station means located in said activity plane substantially without contamination.

30. A blister processing apparatus for testing a sample of liquid, said apparatus comprising:
a sandwich including two smooth plastic films having a space between them, said space between them being filled with an inert liquid having grease-like characteristics, said space further containing a plurality of process station means;
a blister forming means for producing a blister of said sample in the space between said film;
a substantially rigid plate means for supporting said sandwich; and,
an external pusher means adapted to extert force upon said sandwich against said plate and to move said blister to any of said plurality of process station means,
wherein said sample is introduced into said space by said blister forming means and then moved selectively around said space under the influence of said external pusher means thereby causing said blister to pass through said process station means.

* * * * *